United States Patent
Odaka et al.

(10) Patent No.: US 6,200,958 B1
(45) Date of Patent: Mar. 13, 2001

(54) AGENT FOR TREATING HIGH-RISK IMPAIRED GLUCOSE TOLERANCE

(75) Inventors: Hiroyuki Odaka, Kobe; Ichiro Nakaoka, Hirakata; Yoshiharu Suzuki, Suita, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/347,028

(22) Filed: Jul. 2, 1999

Related U.S. Application Data

(63) Continuation of application No. PCT/JP98/05572, filed on Dec. 9, 1998.

(30) Foreign Application Priority Data

Dec. 10, 1997 (JP) .................................................. 9-339686

(51) Int. Cl.⁷ .............................................. A61K 31/7008
(52) U.S. Cl. ............................................................ 514/42
(58) Field of Search .................................................. 514/42

(56) References Cited

U.S. PATENT DOCUMENTS 4,519,942   5/1985   Yamaoka et al. .................... 252/520

FOREIGN PATENT DOCUMENTS

| | | |
|---|---|---|
| 0 044 981 | 2/1982 | (EP) . |
| 0 049 981 | 4/1982 | (EP) . |
| 0 056 194 | 7/1982 | (EP) . |
| 0 089 812 | 9/1983 | (EP) . |

OTHER PUBLICATIONS

Holman: Diabetes Res. Clin. Pract., 40, Suppl. S21–5 (Jul. 1998).
Shinozaki et al., Metabolism, 45(6), 731–7, (Jun. 1996).
Kawamori et al., Nippon Rinsho, 54(19), 2750–3 (Oct. 1996).
Chiasson et al., Diabetes Care, 19(11), 1190–3, (Nov. 1996).
Mori et al., Diabetes Front., 7(4), 422–424 (1996).
DeBouno et al., Nutrition Research, 9(9), 1041–52 (1989).
Inoue et al., Diabetes Res. Clin. Pract., 36, 143–151 (1997).
C. Ito, "IGT as a Risk Factor for the Development of Diabetes", Diabetes Frontier: 136, 1992.
Madar et al., Nutrition Research, 11(9), 1035–46 (1991).
Yamauchi et al., Jpn. Pharmacl. Ther. [Yakuri to Choryl], 24(5), 1103–1107 (1996).
Takami et al., Jpn. Pharmacl. Ther. [Yakuri to Choryl], 19(11), 4456–4467 (1991).
Odaka et al., Nippon Eiyo, Shokuryo Gakkaishi, 45(1), 33–38 (1992).

*Primary Examiner*—Phyllis G. Spivack
(74) *Attorney, Agent, or Firm*—Wenderoth, Lind & Ponack, L.L.P.

(57) ABSTRACT

The present invention discloses an α-glucosidase inhibitor for prevention of transition from high-risk IGT to diabetes mellitus, for prophylaxis of diabetes mellitus, as well as for treating high-risk IGT.

9 Claims, No Drawings

AGENT FOR TREATING HIGH-RISK IMPAIRED GLUCOSE TOLERANCE

This application is a continuation application under 35 USC §111 of PCT International Appln. No. PCT/JP98/05572 filed Dec. 9, 1998.

TECHNICAL FIELD

The present invention relates to an agent for treating high-risk impaired glucose tolerance, especially to an agent for prevention of transition from high-risk impaired glucose tolerance to diabetes mellitus. The present agent is useful in therapeutic fields of the diabetes mellitus or high-risk impaired glucose tolerance.

BACKGROUND ART

According to the criteria issued by WHO (World Health Organization) based on a glucose tolerance test, diabetes mellitus and impaired glucose tolerance (hereinafter sometimes referred to as IGT) are distinguished by the fasting blood glucose level and the blood glucose level 2 hours after glucose loading. Patients with IGT have high blood glucose levels compared to those of patients with diabetes mellitus, and are reported to be at increased risk of developing diabetes mellitus and complications of arteriosclerotic diseases. In particular, it is known that patients with IGT who have blood glucose levels of 170 mg/dl or above at 2 hours following glucose loading, i.e., patients with high-risk IGT, may develop diabetes mellitus at a high rate [Diabetes Frontier, p. 136, 1992].

With regard to voglibose which is an α-glucosidase inhibitor, there are reports of studies on effects of voglibose for insulin-resistant IGT and diabetes [Yakuri-to-Chiryo (Japanese Pharmacology & Therapeutics), 24 (5):213 (1996); Metabol. Exp. Clin., 45:731, 1996].

Voglibose (AO-128) is also known to have effects of lowering blood glucose level and improving glucose tolerance in rats [Yakuri-to-Chiryo (Japanese Pharmacology & Therapeutics), 19 (11):161 (1991); Journal of Nutrition Science and Vitaminology, 45 (1): 33 (1992)]. On the contrary, it has also been reported that the effect of voglibose in improving glucose tolerance could not be verified in human [Rinsho-Seijinbyo, 22 (4): 109 (1992)].

For the above-mentioned high-risk IGT, in particular, there have been no report so far about research for preventing its transition to diabetes mellitus or about its treatment to recover the normal condition.

DISCLOSURE OF INVENTION

The present invention aims to develop an agent for prevention of transition from high-risk IGT to diabetes mellitus, used as a prophylaxis for diabetes mellitus, as well as an agent for treating high-risk IGT.

The present invention relates to:

(1) An agent for prevention of transition from high-risk impaired glucose tolerance to diabetes mellitus comprising an α-glucosidase inhibitor;

(2) An agent for treating high-risk impaired glucose tolerance comprising an α-glucosidase inhibitor;

(3) The agent of the above items (1) or (2) wherein α-glucosidase inhibitor is voglibose.

(4) The agent of the above items (1), (2) or (3) wherein the high-risk impaired glucose tolerance exhibits a blood glucose level between 170 and 199 mg/dl at 2 hours in a 75 g oral glucose tolerance test;

(5) The agent of the above item (2) or (3) which is administered until the blood glucose level at 2 hours in a 75 g oral glucose tolerance test decreases to the normal range;

(6) The agent of the above items (1), (2) or (3) for administering for 13 weeks or longer;

(7) The agent of the above item (1) or (3) wherein the diabetes mellitus is non-insulin-dependent diabetes mellitus;

(8) The agent of the above items (1), (2) or (3) which is in the form of preparation for oral administration;

(9) The agent of the above item (1), (2) or (3) which is administered at a dose of 0.15 to 15 mg per day;

(10) The agent of the above item (1), (2) or (3) which is administered within 60 minutes before meals.

(11) A method of treatment of IGT or prevention of IGT from progressing to diabetes mellitus which comprises administering the agent of item (1) to (10).

(12) Use of α-glucosidase inhibitor for treatment of IGT or prevention of IGT from progressing to diabetes mellitus which comprises administering the agent of item (1) to (10).

(13) Use of α-glucosidase inhibitor in the manufacture of medicament for the treatment of IGT or the prevention of IGT from progressing to diabetes mellitus which comprises administering the agent of item. (1) to (10).

α-Glucosidase inhibitors used in the present invention are those agents which have effects of inhibiting digestive enzymes such as amylase, maltase, α-dextrinase, and sucrase, and thereby retarding digestion of starch and sucrose.

As these types of pharmaceutical compounds are mentioned, for instance, valiolamine derivatives of the general formula;

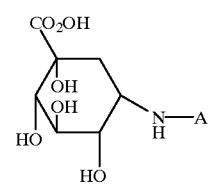

[I]

wherein A stands for a $C_{1-10}$ acyclic hydrocarbon group which may be substituted by hydroxyl, phenoxy, thienyl, furyl, pyridyl, cyclohexyl or optionally substituted phenyl, a $C_{5-6}$ cyclic hydrocarbon group which may be substituted by hydroxyl, hydroxymethyl, methyl or amino, or a sugar residue. They are described in U.S. Pat. Nos. 4,701,559; 4,777,294; 4,595,678, and Japanese Patent Application KOKAI Nos. 200335/1982; 59946/1983; 162597/1983; 216145/1983; 73549/1984; 95297/1984.

Referring to the above general formula [I], A includes a $C_{1-10}$ straight chain or branched aliphatic hydrocarbon group which may be either saturated or unsaturated, and these may be substituted by hydroxy, phenoxy, thienyl, furyl, pyridyl, cyclohexyl, or phenyl which may be substituted. The substituents for the phenyl group which may be substituted includes lower alkyl (e.g., $C_{1-6}$), lower alkoxy (e.g., $C_{1-6}$), halogen (for example, fluorine, chlorine, bromine, iodine), phenyl and so on.

Furthermore, A stands for a $C_{5-6}$ cyclic hydrocarbon group or a sugar residue. These groups may be substituted with hydroxy, hydroxymethyl, methyl, or amino. The term 'sugar residue' means herein the remaining group on removal of one hydrogen atom from a saccharide molecule, and as such may stand for the residue derived from a monosaccharide or an oligosaccharide, for instance.

These derivatives may be used in the form of salts with inorganic acids, e.g. hydrochloric acid, or organic acids, e.g. citric acid.

The following is a partial list of valiolamine derivatives represented by the general formula [I].

(1) N-phenethylvaliolamine,
(2) N-(3-phenylallyl)valiolamine,
(3) N-furfurylvaliomine,
(4) N-thienylvaliolamine,
(5) N-(3-pyridylmethyl)valiolamine,
(6) N-(4-bromobenzyl)valiolamine,
(7) N-[(R)-β-hydroxyphenethyl]valiolamine,
(8) N-[(S)-β-hydroxyphenethyl]valiolamine,
(9) N-(β-hydroxy-2-methoxyphenethyl)valiolamine,
(10) N-(3,5-di-tert-butyl-4-hydroxybenzyl)valiolamine,
(11) N-(cyclohexylmethyl)valiolamine,
(12) N-geranylvaliolamine,
(13) N-(1,3-dihydroxy-2-propyl)valiolamine,
(14) N-(1,3-dihydroxy-1-phenyl-2-propyl)valiolamine,
(15) N-[(R)-α-(hydroxymethyl)benzyl]valiolamine,
(16) N-cyclohexylvaliolamine,
(17) N-(2-hydroxycyclohexyl)valiolamine,
(18) N-[(1R,2R)-2-hydroxycyclohexyl]valiolamine,
(19) N-(2-hydroxycyclopentyl)valiolamine,
(20) methyl 4-[(1S,2S)-(2,4,5(OH)/3,5)-2,3,4,5-tetrahydroxy-5-(hydroxymethyl)cyclohexyl]amino-4,6-dideoxy-α-D-glucopyranoside,
(21) methyl 4-[(1S,2S)-(2,4,5(OH)/3,5)-2,3,4,5-tetrahydroxy-5-(hydroxymethyl)cyclohexyl]amino-4-deoxy-α-D-glucopyranoside,
(22) [(1S,2S)-(2,4,5(OH)/3,5)-2,3,4,5-tetrahydroxy-5-(hydroxymethyl)cyclohexyl][(1R,2S)-(2,6/3,4)-4-amino-2,3-dihydroxy-6-(hydroxymethyl)cyclohexyl]amine,
(23) N-[(1R,2S)-(2,4/3,5)-2,3,4-trihydroxy-5-(hydroxymethyl)cyclohexyl]valiolamine,
(24) N-[(1R,2S)-(2,6/3,4)-4-amino-2,3-dihydroxy-6-methylcyclohexyl]valiolamine,
(25) N-[(1R,2S)-(2,6/3,4)-2,3,4-trihydroxy-6-methylcyclohexyl]valiolamine,
(26) N-[(1R,2S)-(2,4,6/3)-2,3,4-trihydroxy-6-methylcyclohexyl]valiolamine,
(27) 4-O-α-[4-[((1S)-(1,2,4,5(OH)/3,5)-2,3,4,5-tetrahydroxy-5-(hydroxymethyl)cyclohexyl)amino]-4,6-dideoxy-D-glucopyranosyl]-D-gluopyranose, and
(28) 1,6-anhydro-4-O-α-[4-[((1S)-(1,2,4,5(OH)/3,5)-2,3,4,5-tetrahydroxy-5-C-(hydroxymethyl)cyclohexyl)amino]-4,6-dideoxy-D-glucopyranosyl]-β-D-glucopyranose.

Among these, a preferred compound for the purpose of this invention is N-(1,3-dihydroxy-2-propyl)valiolamine, i.e. [2-hydroxy-1-C-(hydroxymethyl)ethyl ]valiolamine or 1L(1S)-(1(OH),2,3,5,/1,3)-5-[[2-hydroxy-1-(hydroxymethyl)ethyl]amino]-1-C-(hydroxymethyl)-1,2,3,4-cyclohexanetetrol(hereinafter, sometimes referred to voglibose).

Further α-glucosidase inhibitors are N-substituted derivatives of valienamine of the general formula of

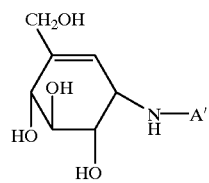

[wherein A' is a $C_{1-10}$ acyclic hydrocarbon group which may be substituted by hydroxyl, phenoxy, thienyl, furyl, pyridyl, cyclohexyl, or phenyl optionally substituted by substituents described for A above, such as lower alkyl (e.g. $C_{1-6}$), lower alkoxy (e.g. $C_{1-6}$), halogen, phenyl and so on, a $C_{5-6}$ cyclic hydrocarbon group which may be substituted by hydroxyl, hydroxymethyl, methyl or amino, or a sugar residue]which is described in U.S. Pat. No. 4,486,602, and Japanese Patent Application KOKAI No. 64648/1982.

A N-substituted derivative of validamine represented for the general formula,

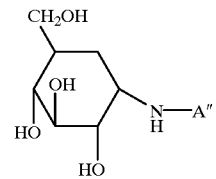

[wherein A" is a $C_{1-10}$ acyclic hydrocarbon group which may be substituted by hydroxyl, phenoxy, thienyl, furyl, pyridyl, cyclohexyl, or phenyl optionally substituted by the same substituents defined for A or A' above, a $C_{5-6}$ cyclic hydrocarbon group which may be substituted by hydroxyl, hydroxymethyl, methyl or amino, or a sugar residue] which is described in U.S. Pat. Nos. 4,701,559; 4,777,294, and Japanese Patent Application KOKAI No. 114554/1982 can also be used preferably as α-glucosidase inhibitors. Additionally the following compounds can be used as an α-glucosidase inhibitor for the purposes of this invention.

Acarbose (BAY g 5421, Naturwissenschaften 64, 535–537, 1997, U.S. Pat. No. 4,062,950, and Japanese Patent Application KOKOKU 39474/1979); trestatin (J. Antibiotics 36, 1157–1175, 1983 and 37, 182–186, 1984 and U.S. Pat. No. 765 and Japanese Patent Application KOKAI 163511/1979), adiposins (J. Antibiotics 35, 1234–1236, 1982), J. Jap. Soc. Starch Sci 26, 134–144(1979), 27, 107–113, 1980, Japanese Patent Application KOKAI No. 106402/1979; No. 106403/1979; No. 64509/1980; No. 123986/1981 and No. 125398/1981, and U.S. Pat. No. 4,197,292), amylostatins (Agric. Biol. Chem. 46, 1941–1945, 1982, Japanese Patent Application KOKAI Nos. 123891/1975; 71494/1980; 157595/1980 and U.S. Pat. No. 4,010,258), oligostatins (SF-1130X, Japanese Patent Application KOKAI Nos. 43294/1981; 3294/1981 and U.S. Pat. No. 4,316,894, J. Antibiotics 34, 1424–1433, 1981), and aminosugar compounds (U.S. Pat. No. 4,254,256 and Japanese Patent Application KOKAI No. 92909/1979).

Regarding the α-glucosidase inhibitors of microbial origin, inclusive of the above-mentioned compounds, a general review by E. Truscheit (Angewandte Chemie 93, 738–755, 1981) is available.

Furthermore, the compounds obtainable by methanolysis of acarbose or oligostatins C, i.e. methyl 4-[(1S,6S)-(4,6/5)-4,5,6-trihydroxy-3-hydroxymethyl-2-cyclohexen-1-yl ]

amino4,6-dideoxy-α-D-glucopyranosides [182nd ACS National Meeting Abstracts Paper, MEDI 69, August 1981, New York, J. Antibiotics 34, 1429–1433, 1981, and Japanese Patent Application KOKAI No. 24397/1982], 1-deoxynojirimycin (Naturwissenschaften 66, 584–585, 1979) and N-substituted derivatives thereof, for instance, miglitol (BAY m 1099) and BAY o 1248 (J. Clin. Invest. 14 (2-II), 47, 1984; Diabetologia 27 (2), 288A, 346A and 323A, 1984) can also be used as α-glucosidase inhibitors.

These α-glucosidase inhibitors may be used alone or in combination with one or more other such inhibitors.

Preferably, the α-glucosidase inhibitor used in the present invention is voglibose, acarbose, or miglitol, and voglibose is particularly preferred.

WHO (World Health Organization) has proposed criteria, in connection with the definition of "impaired glucose tolerance" based on a 75 g oral glucose tolerance test (75 g-OGTT). According to the criteria, "impaired glucose tolerance" is such a condition in which the Fasting Blood Glucose level (venous plasma) is below 140 mg/dl and the blood glucose level (in venous plasma) 2 hours after a 75 g-OGTT, which test is conducted after overnight fasting, is 140–199 mg/dl.

The term "high-risk impaired glucose tolerance" as used herein means such a condition in which the fasting blood glucose level (venous plasma) is below 140 mg/dl and the blood glucose level at 2 hours in 75 g-OGTT conducted after overnight fasting is 170–199 mg/dl.

On the other hand, diabetes mellitus is a condition in which the fasting blood glucose level (venous plasma) is 140 mg/dl or above and the blood glucose level at 2 hours in the above-mentioned 75 g-OGTT is 200 mg/dl or above. There are various types of diabetes mellitus including, for example, insulin-dependent diabetes mellitus (type-1; IDDM) and non-insulin-dependent diabetes mellitus (type-2; NIDDM), and the pharmaceutical composition of the present invention is suitably used, in particular, against non-insulin-dependent diabetes mellitus.

For the purpose of the present invention, "treating" means such a treatment of high-risk impaired glucose tolerance by which the blood glucose level at 2 hours in 75 g-OGTT conducted after overnight fasting is lowered to the normal range.

The "normal range" means either that the Fasting Blood Glucose level (venous plasma) is below 110 mg/dl or that the blood glucose level at 2 hours in 75 g-OGTT after overnight fasting is below 140 mg/dl, or both.

On the other hand, "prevention of transition" means prevention of transition in blood glucose levels from those observed in patients with high-risk IGT as defined above to those observed in patients with diabetes mellitus as defined above, and it is not necessary to lower the two kinds of blood glucose level mentioned above to their normal ranges.

Although α-glucosidase inhibitors may be used alone, they are usually used as a pharmaceutical composition prepared with other ingredients such as a pharmacologically acceptable carrier by known methods.

The pharmaceutical compositions used for the present invention may be prepared by conventional methods in the art, for example, those described in the Japanese Pharmacopoeia (e.g. the 13th revision). Some of the dosage forms of the present compositions may be, for example, those for oral administration such as tablet, capsule (including soft capsule and microcapsule), powder, pellet, granule, and syrup, or those for non-oral administration such as injection, and suppository, and they may be administered orally or non-orally, respectively. In addition to these regular dosage forms, an oral disintegrable solid formulation (e.g., tablet, granule, and fine granule) and a sustained-release preparation for oral or non-oral administration (tablet, granule, fine granule, pill, capsule, syrup, emulsion, suspension, solution) can be also applied to the present invention. These formulations can be also prepared by conventional methods. It is particularly preferred that the pharmaceutical formulations for the present invention are those for oral administration.

The pharmacologically acceptable carrier used herein is any of various organic or inorganic carriers conventionally used as pharmaceutical materials individually, or in combination. They are used as excipients, lubricants, binders, disintegrators, acids, foaming agents, stabilizers, coating agents and the like for solid formulations, or as solvents, solubilizers, suspending agents, isotonic agents, buffers, soothing agents, emulsifiers and the like for liquid formulations. In addition, other additives such as antiseptic agents, antioxidants, colorants, sweeteners, and flavorants may also be used as needed.

Preferred examples of excipients include, for example, lactose, sucrose, D-mannitol, xylitol, sorbitol, erythritol, starch, crystalline cellulose, and light anhydrous silicic acid.

Preferred examples of lubricants include, for example, magnesium stearate, calcium stearate, talc, colloidal silica, sucrose fatty acid ester, polyethyleneglycol, stearic acid, etc.

Preferred examples of binders include, for example, pregelatinized starch, methyl cellulose, crystalline cellulose, sucrose, D-mannitol, trehalose, dextrin, hydroxypropylcellulose, hydroxypropylmethylcellulose, polyvinylpyrrolidone, gum arabic powder, gelatin, pullulan, etc. The use of crystalline cellulose as the binders provides a solid preparation which exhibit excellent composition strength properties while retaining excellent fast disintegration properties. Such crystalline cellulose includes microcrystalline cellulose. Examples of the crystalline cellulose include CEOLUS KG801, avicel PH101, avicel PH102, avicel PH301, avicel PH302, avicel RC-A591NF (crystalline cellulose carmellose sodium), etc.

Preferred examples of disintegrators include, for example, starch, carboxymethylcellulose, low-substituted-hydroxypropylcellulose, carboxymethylcellulose calcium, crospovidone [manufactured by ISP Inc. (U.S.A.), BASF (Germany)], croscarmellose sodium [FMC-Asahi Chemical Co., Ltd. (Japan)], carmellose calcium [Gotoku Chemical (Yakuhin), (Japan)]; hydroxypropylcellulose; carboxymethylstarch sodium [Matsutani Chemical Co., Ltd. (Japan)]; corn starch, etc., with preference given to crospovidone. Two or more of these disintegrators can be as a mixture in a given ratio. As crospovidone, any cross-linked homopolymer called 1-ethenyl-2-pyrrolidinone homopolymer may be used, and usually crospovidone having a molecular weight of at least 1,000,000 is used. Specific examples of crospovidone available as a product on the market include Cross-linked povidone, Kollidon CL [manufactured by BASF (Germany)], Polyplasdone XL, Polyplasdone XL-10, INF-10 [manufactured by ISP], polyvinylpolypyrrolidone, PVPP and 1-vinyl-2-pyrrolidinone homopolymer. The disintegrator is used, for instance, in an amount of 0.1 to 20 weight parts, preferably 1 to 10 weight parts, per 100 weight parts of a solid preparation.

Preferred examples of the acids include citric acid, tartaric acid, malic acid, etc.

Preferred examples of the foaming agents include sodium hydrogen carbonate, etc.

Preferred examples of the stabilizers include a basic substance in the case of a basic pharmaceutically active ingredient.

Preferred examples of the solvent include, for example, water-for-injection, alcohols, propylene glycol, macrogols, sesame oil, corn oil, and tricaprilin.

Preferred examples of the solubilizers include, for example, polyethylene glycols, propylene glycol, D-mannitol, trehalose, benzyl benzoate, ethanol, trisaminomethane, cholesterol, triethanolamine, sodium carbonate, and sodium citrate.

Preferred examples of the suspending agent include, for example, surfactants such as stearyltriethanolamine, sodium lauryl sulfate, laurylaminopropionic acid, lecithin, benzalkonium chloride, benzethonium chloride, and glyceryl monostearate; and hydrophilic polymers such as polyvinyl alcohol, polyvinylpyrrolidone, carboxymethyl cellulose sodium, methylcellulose, hydroxymethyl cellulose, hydroxyethyl cellulose, and hydroxypropyl cellulose.

Preferred examples of the isotonic agent include, for example, sodium chloride, glycerin, and D-mannitol.

Preferred examples of the buffer include, for example, buffer solutions comprising phosphate, acetate, carbonate, citrate, or the like.

Preferred examples of the soothing agent include, for example, benzyl alcohol.

The emulsifiers which provide a stable O/W emulsion can be used generally. Preferred examples of such emulsifiers include anionic surfactants (e.g., sodium oleate, sodium stearate, sodium lauryl sulfate), nonionic surfactants (e.g., Tween 80, Tween 60, HCO-60, HCO-70), polyvinyl alcohol, polyvinylpyrrolidone and gelatin. Two or more of these emulsifiers may be used in combination in an appropriate ratio. The emulsifier concentration in an external aqueous phase ranges for instance from 0.01 to 20%, preferably from 0.05 to 10%.

Preferred examples of the antiseptic agent include, for example, p-hydroxybenzoic acid esters, chlorobutanol, benzyl alcohol, phenethyl alcohol, dehydroacetic acid, and sorbic acid.

Preferred examples of the antioxidant include, for example, sulfite and ascorbic acid.

Preferred examples of the colorants include various food colorants (e.g. Food Yellow No. 5, Food RED No. 2, Food Blue No. 2, etc.), food lakes, red iron oxide, and dyes such as titanium oxide.

Preferred examples of the sweeteners include saccharin sodium, dipotassium glycyrrhizinate, aspartame, stevia, thaumatin, etc.

Preferred examples of the flavorants include lemon, lemon lime, orange, menthol, etc.

Preferred examples of the coating agents (for masking the taste and conferring an enteric or sustained-release property) include hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (Rohm Company, Germany, methacrylic acid-acrylic acid copolymer). Espesially, this coating agent can be used for preparing an enteric solid formulation such as granules and fine granules by conventional methods. These enteric formulation can be further applied for preparing tablet, capsule, fast disintegrative tablet and the like.

The above-mentioned fast disintegrable solid formulation used for the present invention may comprise (1) α-glucosidase inhibitor, (2) one or more water-soluble sugar alcohol selected from the group consisting of sorbitol, maltitol, reduced starch saccharide, xylitol, reduced paratinose and erythritol (hereafter also referred to as a water-soluble sugar alcohol), and (3) low-substituted hydroxypropylcellulose having hydroxypropoxyl group contents of 7.0 to 9.9 percent by weight.

In this fast disintegrable formulation, the α-glucosidase inhibitor can be coated, by the per se known method, for masking the taste and odor or for enteric dissolution or sustained release. The coating material for this formulation includes, for instance, enteric coating polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose, etc.; gastric coating polymers such as polyvinylacetal diethylaminoacetate, aminoalkyl methacrylate copolymer, etc.; water-soluble polymers such as hydroxypropylcellulose, hydroxypropylmethylcellulose, etc.; water-insoluble polymers such as ethylcellulose, aminoalkyl methacrylate copolymer RS, ethylacrylate methylmethacrylate copolymer, etc.; wax, etc.; and the agents mentioned above as the coating agent.

For this formulation, the α-glucosidase inhibitor is used in an amount of 0.01 to 70 weight parts, preferably 0.02 to 50 weight parts, more preferably 0.05 to 30 weight parts, per 100 weight parts of a solid preparation.

The above-mentioned water-soluble sugar alcohol means a water-soluble sugar alcohol which needs water in an amount of less than 30 ml when 1 g of a water-soluble sugar alcohol is added to water and dissolved within about 30 minutes at 20° C. by strongly shaking every 5 minutes for 30 seconds. As the water-soluble sugar alcohol, sorbitol, maltitol, reduced starch saccharide, xylitol, reduced paratinose or erythritol is employed. Two or more of these water-soluble sugar alcohols can be used as a mixture in a given ratio. The water-soluble sugar alcohol is preferably xylitol or erythritol, especially preferably erythritol. As erythritol, one that is produced by fermentation with yeasts using glucose as the starting material, and that has a particle size of at most 50 mesh is used. Such erythritol is available as a product on the market such as a product manufactured by Nikken Chemical Co., Ltd.(Japan). The water-soluble sugar alcohol is used in an amount of 5 to 97 weight parts, preferably 10 to 90 weight parts, per 100 weight parts of a solid preparation.

The hydroxypropoxyl group contents of the said low-substituted hydroxypropylcellulose employed in the present invention range from 7.0 to 9.9 percent by weight. Examples of the low-substituted hydroxypropylcellulose having hydroxypropoxyl group contents of 7.0 to 9.9 percent by weight include LH-22, LH-32, and mixtures thereof. These are available as products on the market, manufactured, e.g., by Shin-Etsu Chemical Co., Ltd.(Japan). The low-substituted hydroxypropylcellulose having hydroxypropoxyl group contents of 7.0 to 9.9 percent by weight is used in an amount of 3 to 50 weight parts, preferably 5 to 40 weight parts, per 100 weight parts of a solid preparation. In the fast disintegration in a solid preparation, it is preferable to use low-substituted hydroxypropylcellulose having hydroxypropoxyl group contents of 7.0 to 9.9 percent by weight. The fast disintegrable formulation is useful especially as a preparation which is capable of fast disintegration, and administered without water or together with water. Its form includes tablets, granules, fine granules, etc., with preference given to tablets.

The fast disintegrable solid formulation may further contain a variety of additives which are commonly employed in the manufacture of preparations in general dosage forms. The amount of such additives to be used are those commonly employed in the manufacture of preparations in general dosage forms. Such additives include, for instance, binders, acids, foaming agents, artificial sweeteners, flavorants, lubricants, colorants, stabilizers, disintegrators, etc. These are ones commonly-used in the pharmaceutical field as mentioned above.

The molding procedure of the fast disintegrable formulation can be a conventional method and it can be carried out, for instance, by tabletting with a pressure of 0.5 to 3 ton/cm$^2$ by using a single-punch tabletting machine or a rotary type tabletting machine with appropriate materials mentioned above when the solid preparation is a tablet. The drying procedure can be carried out by any of the techniques used commonly in the art, such as vacuum drying, fluidized-bed drying, etc.

The sustained-release dosage form can be prepared by a conventional method. For example, in case of an oral sustained-release formulation, it can be in the form of tablet, capsule, granules, fine granules and the like. Preferably it is in the form of granules or capsule containing the granules. For the said formulation, to achieve such sustained-release effect, a matrix having the features of staying in digestive tubes such as small or large intestines, stomach, rectum and the like for a long time period is used. The matrix is polyglycerolic fatty acid ester or a mixture of the ester and lipid with a mp in the range of 30 to 120° C., preferably 40 to 120° C. Preferably, a viscous substance such as a natural or synthetic polymer is dispersed in the matrix or the matrix is coated with such viscous substances. The said polyglycerolic fatty acid ester can be mono-, di- or tri-ester. It is constituted by a polyglycerol having about 2 to 20 degree of polymerization and fatty acid having 12 to 22 carbon atoms. The fatty acid is usually unsaturated fatty acid such as stearic acid and the like. As the lipid, conventional substances ordinarily used as lipids can be used. It is exemplified by a saturated fatty acid having 14 to 22 carbon atoms, such as palmitic acid and the like or its salts. The viscous substance is exemplified by a natural viscous polymer such as gelatin, cardlan, gums and the like, and a synthetic viscous polymer such as carboxyvinylpolymer, acrylic polymer and the like. The ratio of these ingredients can be appropriately determined in order that the formulation can achieve the sustained-release effect. Production methods for the sustained-release polymer are exemplified by spraydrying and the like. An amount of active ingredient of α-glucosidase inhibitor is in the range of 0.05 to 5.0%(w/w) per total weight of the formulation. The formulation usually stays in the digestive tubes for 3 to 20 hours. In this formulation, it is administered one or two times a day.

The pharmaceutical compositions used for the present invention have low toxicity, and therefore, can be administered safely to mammals (e.g., human, mouse, rat, rabbit, canine, cat, bovine, equine, swine, monkey, and the like).

The dose of the pharmaceutical compositions of the present invention is selected as appropriate according to the subject to be treated, the dosage form, the method of administration, and the like. Such dose is selected so that the effective amount of α-glucosidase inhibitor, in particular, the dose of the above-mentioned valiolamine derivatives such as voglibose, is usually 0.15–15 mg/day, preferably 0.2–1.5 mg/day, and more preferably 0.3–0.9 mg/day, for oral administration. In the case of the oral sustained-release dosage form, it should be administered in the way that the active ingredient amount per day is in the range of the above-mentioned dose. In case of the non-oral administration, its administration dose depends upon the dosage form. In any case, the dose is a pharmaceutically-effective amount which is enough for the dosage form to show the same pharmaceutical efficacy as the oral formulation.

Frequency of administration varies depending on the dosage form. For example, oral dosage forms such as tablet, capsule, powder, granule, syrup and an oral disintegrable formulation (tablet, capsule, etc.) are administered one to three times per day, preferably three times a day; the sustained-release preparation, once per the predetermined period for the formulation, conventionally once a day. The formulation is usually administered within 60 minutes before a meal, preferably within 30 minutes before a meal, and more preferably within 5 minutes before a meal. For any kind of the oral dosage form, it is preferably administered before a meal.

On the other hand, non-oral dosage forms such as injection and suppository are administered less than once per day. The sustained-release non-oral preparation is administered once per predetermined period for the formulation. Generally the formulation is not necessarily administered before a meal.

Although it is depended upon an individual patient, in general an administration period for any formulation is preferably 13 weeks or longer, more preferably 20 weeks or longer, and much more preferably for 28 weeks or longer in order to achieve the purpose of this invention.

Such administration is preferably continuous. As long as the administration is substantially continuous, daily administration is not necessary. This means that the administration of the agent should be repeated within a short period enough to have the agent continuously show the effect of this invention. For example, once every another day administration or the like. In case of an intermittent administration, the interval period of administration is usually as long as two weeks or longer, but the period shorter than two weeks is also probable.

BEST MODE FOR CARRYING OUT THE INVENTION

The present invention is described in more detail with reference to the following Examples. The present invention, however, is not limited to such Examples in any way.

EXAMPLES

Example 1

According to conventional procedures, tablets comprising the following ingredients are prepared.

| (Contents per one tablet) | |
| --- | --- |
| Voglibose | 0.3 mg |
| Corn starch | 35.0 mg |
| Hydroxypropyl cellulose | 5.8 mg |
| Magnesium stearate | 0.6 mg |
| Lactose | q.s. |
| Total | 200.0 mg |

Example 2

According to conventional procedures, tablets comprising the following ingredients are prepared.

| (Contents per one tablet) | |
| --- | --- |
| Voglibose | 0.2 mg |
| Corn starch | 23.0 mg |
| Hydroxypropyl cellulose | 0.4 mg |
| Magnesium stearate | 0.6 mg |
| Lactose | q.s. |
| Total | 130.0 mg |

Test 1

Voglibose (0.6 mg/day, 0.2 mg each before meals, tablet) was administered for 28 weeks to each of Patients A (female, 62 years old), B (male, 68 years old), and C (male, 53 years old) having high-risk impaired glucose tolerance. In each case, 75 g oral glucose tolerance tests (hereinafter referred to as OGTTs) were conduced before and after the period of voglibose administration.

The results of such OGTTs conducted before and after the period of voglibose administration are shown in Tables 1 and 2, respectively.

TABLE 1

Blood glucose level before the period of voglibose administration (mg/dl)

| Patient | Before OGTT | 2-h level in OGTT | Difference |
| --- | --- | --- | --- |
| A | 136 | 186 | 50 |
| B | 128 | 178 | 50 |
| C | 127 | 196 | 69 |

TABLE 2

Blood glucose level after the period of voglibose administration (mg/dl)

| Patient | Before OGTT | 2-h level in OGTT | Difference |
| --- | --- | --- | --- |
| A | 135 | 172 | 37 |
| B | 118 | 138 | 20 |
| C | 122 | 157 | 35 |

As shown in Table 1, the blood glucose levels of Patients A, B, and C at 2 hours in OGTTs were 186, 178, and 196 mg/dl, respectively, and thus were all between 170 and 199 mg/dl. In other words, all the patients had high-risk impaired glucose tolerance.

As also apparent from comparison between Tables 1 and 2, glucose tolerance of the patients with high-risk impaired glucose tolerance had been remarkably improved by administration of voglibose.

Specifically, the blood glucose levels at 2 hours in OGTTs for the Patients A, B and C who had high-risk impaired glucose tolerance before the administration of voglibose were 172, 138, and 157 mg/dl, respectively, after the period of voglibose administration, and thus were all below 200 mg/dl, as shown in Tables 1 and 2. Furthermore, the impaired glucose tolerance was improved in one case to the normal range below 140 mg/dl. Thus, transition from high-risk glucose tolerance to diabetes mellitus was not observed in this test, and the treatment exhibited even an effect of lowering the blood glucose level in the 2-h OGTT to the normal range below 140 mg/dl.

Effects of the Invention

The agents of the present invention shows excellent effect on prevention of transition from high-risk impaired glucose tolerance, which may progress to diabetes mellitus at a high rate, to diabetes mellitus, and therefore, are useful as prophylactics for diabetes mellitus. The present agents may also be useful as therapeutics for high-risk impaired glucose tolerance. The agents of the present invention have low toxicity, and therefore, can be administered safely to mammals, in particular, to human.

What is claimed is:

1. A method of preventing transition from high-risk impaired glucose tolerance exhibiting a blood glucose level between 170 and 199 mg/dl at 2 hours in a 75 g oral glucose tolerance test to diabetes mellitus exhibiting a blood glucose level of 200 mg/dl or above at 2 hours in a 75 g oral glucose tolerance test in a mammal in need thereof, which comprises administering to said mammal an effective amount of α-glucosidase inhibitor within 60 minutes before a meal for 13 weeks or longer.

2. The method as claimed in claim 1 wherein the diabetes mellitus is non-insulin-dependent diabetes mellitus.

3. A method of treating high-risk impaired glucose tolerance exhibiting a blood glucose level between 170 and 199 mg/dl at 2 hours in a 75 g oral glucose tolerance test in a mammal in need thereof, which comprises administering to said mammal an effective amount of α-glucosidase inhibitor within 60 minutes before a meal for 13 weeks or longer and until the blood glucose level at 2 hours in a 75 g oral glucose tolerance test decreases to the level below 140 mg/dl.

4. The method as claimed in claim 1 or 3 wherein the α-glucosidase inhibitor is voglibose.

5. The method as claimed in claim 1 or 3 wherein the α-glucosidase inhibitor is acarbose.

6. The method as claimed in claim 1 or 3 wherein the α-glucosidase inhibitor is in a dosage form for oral administration.

7. The method as claimed in claim 1 or 3 wherein the administration dose is in the range of 0.15 to 15 mg per day.

8. The method as claimed in claim 1 or 3 wherein the α-glucosidase inhibitor is administered for 20 weeks or more.

9. The method as claimed in claim 1 or 3 wherein the α-glucosidase inhibitor is administered for 28 weeks or more.

* * * * *